United States Patent
Xu et al.

(10) Patent No.: US 7,801,597 B2
(45) Date of Patent: Sep. 21, 2010

(54) METHOD AND APPARATUS FOR BRAIN WAVE FLUCTUATIONS ANALYSIS

(75) Inventors: Jianlan Xu, Guangzhou (CN); Enhong Liu, Guangzhou (CN)

(73) Assignee: Guangzhou Kefu Medical Technology Co., Ltd, Guangzhou (CN)

( * ) Notice: Subject to any disclaimer, the term of this patent is extended or adjusted under 35 U.S.C. 154(b) by 1105 days.

(21) Appl. No.: 10/596,537

(22) PCT Filed: Dec. 22, 2004

(86) PCT No.: PCT/CN2004/001493
§ 371 (c)(1),
(2), (4) Date: Jul. 12, 2006

(87) PCT Pub. No.: WO2005/060830
PCT Pub. Date: Jul. 7, 2005

(65) Prior Publication Data
US 2007/0185407 A1    Aug. 9, 2007

(30) Foreign Application Priority Data
Dec. 23, 2003   (CN) ................. 2003 1 0122416

(51) Int. Cl.
*A61B 5/04*   (2006.01)
(52) U.S. Cl. ...................... 600/544; 600/301
(58) Field of Classification Search ............... 600/544
See application file for complete search history.

(56) References Cited

U.S. PATENT DOCUMENTS

| | | | | |
|---|---|---|---|---|
| 4,579,125 A | * | 4/1986 | Strobl et al. | 600/544 |
| 5,357,976 A | * | 10/1994 | Feng | 600/544 |
| 5,458,117 A | * | 10/1995 | Chamoun et al. | 600/547 |
| 5,678,560 A | | 10/1997 | Sakamoto et al. | |
| 6,011,990 A | * | 1/2000 | Schultz et al. | 600/544 |
| 2004/0082876 A1 | * | 4/2004 | Viertio-Oja et al. | 600/544 |
| 2008/0167540 A1 | * | 7/2008 | Korhonen et al. | 600/301 |

FOREIGN PATENT DOCUMENTS

JP    06261873 A    9/1994

* cited by examiner

*Primary Examiner*—Patricia C Mallari
*Assistant Examiner*—Karen E Toth
(74) *Attorney, Agent, or Firm*—Workman Nydegger

(57) ABSTRACT

The present invention applies computer techniques to the power spectrum analysis of brain wave signals, wherein the power spectrum fluctuations of supra-slow wave is obtained by selecting the maximum value of the power amplitude within 0.5 and 50 Hz and performing multiple analysis of the power spectrum and frequency spectrum, and a series of data and parameters are obtained to provide a basis for cerebral functions testing and disease diagnosis by analyzing the fluctuations. The analysis method comprises the analysis of the conventional power spectrum and may also comprises the analysis of the fluctuation signals of brain wave power, fluctuations of brain wave, S pedigree and further multi-item analyses. And the relevant apparatus implementing such method comprises electrodes, brain wave signal amplifier or a brain wave recording box, a Personal Computer, data processor and terminal processors.

19 Claims, 3 Drawing Sheets

METHOD AND APPARATUS FOR BRAIN WAVE FLUCTUATIONS ANALYSIS

FIELD OF THE INVENTION

The present invention relates to diagnosis-oriented medical apparatus, and more particularly, to a method for brain wave fluctuations analysis and a relevant apparatus thereof

BACKGROUND OF THE INVENTION

Theoretically, the information of the physiologic and pathologic situation and the functional activities of both human's and animal's brains could be obtained through a test on the brain wave signals in the same way as electrocardiograms. Today, there are two types of signals used in electroencephalographs, analog signals and digital signals (DS). However, because the brain wave signals are very weak and complicated, even the digital electroencephalographs with higher anti-jamming properties could not meet the demand of clinical medical treatment. Therefore, the significance of electroencephalogram is far lower than that of electrocardiogram.

It is a research achievement of China's aeromedicine to detect and analyze the signals of brain wave fluctuations so as to make a judgment in the functioning situation and the diseases of the brain, which means much more than what common electroencephalogram does in clinical medicine. As a result, it is necessary for the medicinal field to get some methods and relevant apparatus to analyze the signals of brain wave fluctuations thoroughly, comprehensively and precisely. The Chinese patent ZL96244175.9, titled "encephalofluctuo gram technology (ET)", is designed to collect, magnify and regularly sample brain wave signals, digital-analog convert and pre-treat data which is then transmitted to PCs. This invention has improved the brain wave signals collecting technique to a brand new level. But this apparatus could not analyze the collected brain wave signals. Doctors could only get the flexuosity of the brain wave, i.e. the electroencephalogram. And how much information useful for diagnosis doctors could get from the electroencephalogram depends on the doctors' discrimination in the electroencephalogram. Therefore, this technology could still not meet the demand of the clinical medicine.

SUMMARY OF THE INVENTION

An object of the present invention is to provide a method to analyze brain wave signals with PC technique and a relevant apparatus, which can get a series of parameters shown in multiple ways for providing reference in brain functions inspection and disease diagnosis.

Hereinafter, definitions and explanation of the technical and scientific terms and nomenclatures related to the present invention are provided by reference to "New Technique on ET-brain Function Research" (published by National Defense Industrial Press, 1994), written by Lei MEI.

S pedigree: the frequency range for brain wave inspection in the present invention is within supra-slow wave with mHz (milli-HZ) as the unit, which is named as supra-slow pedigree and S pedigree for short. According to its frequency S pedigree can be separately named as S1, S2, S3 etc. For example, the frequency of 1 mHz corresponds to S1, the frequency of 2 mHz corresponds to S2, and likewise other spectrum lines of S pedigree are named.

Fundamental frequency, the several commonly used frequencies such as 1, 2, 3, 4, 5, 6, 7, 11 and 13 mHz which have close relation with neurotransmitter in the brain.

Fundamental pedigree: it is the pedigree corresponding to the fundamental frequency.

Dominant Frequency, dominant spectrum line, optimal value: rank the power values of each frequency in the corresponding lead from high to low, and the frequencies of the anterior n values D1-Dn are called dominant frequencies. Their corresponding spectrum lines are called dominant spectrum lines and the power value of the dominant frequency is called optimal value.

Optimal frequency, optimal spectrum line: the maximum D1 in the dominant frequency of each lead is named as optimal frequency and its corresponding spectrum line is optimal spectrum line.

Continuum frequency: sometimes, the values of the spectrum lines in the dominant frequency zone are continuous, such as 2, 3 and 4 mHz, which are called continuum frequency.

Different frequency: spectrum lines from non-resonance frequencies in S pedigree (the frequency value is a prime number larger than 13) and their frequency multiplication are called different frequencies.

Special frequency: a series of frequencies such as 23 mHz, 27 mHz, 28 mHz and 29 mHz and their harmonic frequencies such as 46 mHz and 54 mHz and so on in S pedigree are special frequencies.

Characteristic lines: lines corresponding to continuum frequency, different frequency, special frequency and optimal frequency are generally called characteristic lines.

A/P, L/R: calculating the ratio of the anterior lead power to the posterior power of each frequency according to the lead space distribution positions such as lead F3 to lead C3, which is called as anterior-to-posterior ratio and written as A/P. Comparing the power values of the leads which are at the same position in the right brain and left brain and calculating the ratio thereof such as lead F3 to lead F4, which is called as left-to-right ratio and written as L/R,.

Fluctuation value: generally refers to the values of each pedigree obtained during the analysis of S pedigree.

The present invention is realized according to the following technical solution.

In this invention, the brain wave signals are first divided into subsections in a certain time interval with computer. Power spectrum of each subsection is then analyzed by selecting the maximal power amplitude within 0.5 and 50 Hz, and then several times of power spectrum analyses and frequency spectrum analyses are performed, and then power spectrum fluctuations within the supra-slow wave can be acquired, after that a series of analyses are performed on said fluctuations and a series of data parameters can be acquired which are shown in values, graphs and curves finally.

In this invention, the analysis of the fluctuations of brain wave includes at least the conventional analysis of brain wave. Also, it could include the analysis of fluctuation signals of the power of brain wave, analysis of brain wave fluctuations and S pedigree which are performed in turn. Error treatment can also be used to correct the spectrum.

In this invention, the analysis method of fluctuation of brain wave signals involves the sampling of brain wave signal as well. Any lead system or lead combination can by used for sampling and electrodes arranging, and the 12 leads from the international standard lead system is preferred, with the optimal electrodes positions of F3, F4, C3, C4, P3, P4, O1, O2, F7, F8, T5, T6.

The detailed procedures and arithmetic for each analysis are described respectively as the following.

The said conventional power spectrum analysis includes the following procedures.

(1) Analyze the power spectrum of the brain wave of a given time length., i.e. to carry out Fourier Transformation directly to the observation data having N sampling points $x_N(n)$ of brain wave $x(n)$, with the result of $X_N(e^{j\omega})$ (2) Make a square of its amplitude which is then divided by N. As the estimate value of the real power spectrum $P(e^{j\omega})$ of $x(n)$, the power spectrum estimated with cyclogram can be expressed as $$P(e^{j\omega}) = \frac{1}{N}|X_N(\omega)|^2.$$

(3) Calculating $X_N(\omega)$ by using the fast Fourier Transformation, which includes $$X_N(k) = \sum_{n=0}^{N-1} x(n) W_N^{nk}, k = 0, 1, \ldots, N-1, W_N = e^{-j\frac{2\pi}{N}}.$$

And the power spectrum can be expressed as $$P(k) = \frac{1}{N}|X_N(k)|^2.$$

The said analysis of the brain wave power fluctuation signals includes the following procedures:

(1) Select window function with small side lobe amplitude and fast attenuation, which is expressed as $$\omega(n) = 0.5 - 0.5\cos\left(\frac{2\pi n}{N}\right), n = 0, 1, \ldots N-1.$$

to cut the brain wave signal $x(n)$ and get $x_N(n)=x(n)\omega(n)$.

(2) Analyze the power spectrum of the above signal $x_N(n)= x(n)\omega(n)$ with the sampling time of T seconds. By FFT calculation, the frequency-domain resolution of the frequency spectrum is 1/T. Then, select the power amplitude P with the maximal energy and its corresponding frequency f.

(3) Divide the time domain brain wave signal with the total time length of N seconds into subsections with the interval of T seconds in time sequence. Then carry out the said conventional power spectrum analysis and fluctuation signal analysis of brain wave power in order to get the fluctuation signal p(n) with the maximal power amplitude and its corresponding frequency fluctuation signals f(n), n=1 . . . n, n=N/T. This shows the fluctuation process of the power and its corresponding maximal amplitude during the whole period.

The said analysis of the fluctuations of the brain wave includes the following procedures:

(1) Analyze the fluctuation signals p(n) of the maximal power amplitude with the length of n points.

(2) Multiply it with Hanning window with the length of n and then carry out power spectrum analysis. Since the unit of the time length is N second, frequency domain resolution is thus 1/N Hz. Select the spectrum lines within a certain frequencies in the analysis result of the power spectrum to form the fluctuations of brain wave.

(3) If the whole sampling time is more than N second, divide it into subsection with N seconds as the unit and then carry out the said conventional power spectrum analysis, analysis of the fluctuation signals of brain wave power and fluctuations of the brain wave for each subsection.

The said S pedigree analysis includes the following procedures:

(1) Find out several dominant lines D1-Dn with the maximal amplitude from the fluctuations of brain wave of each lead and arrange them by a descending order, thus S pedigree of single lead data can be obtained which contains n values.

(2) For all N leads, there are N*n dominant spectrum lines. Add together all the dominant spectrum lines with the same frequency so as to get the general pedigree of the S pedigree.

The above analysis method is called as the first level analysis method in the series methods of fluctuation signal analysis of brain wave in this invention. Based on the first level analysis method, several further analyses which are called the second level analysis can be carried out, including the following 24 items. For the convenience of description, each item is marked with a serial number.

The analyses based on the analysis of fluctuation signals of brain wave power include: (1) calculation of entropy (2) single-frequency competition analysis The analyses based on the S pedigree analysis include: (3) analysis of the general pedigree of S pedigree, (4) analysis of fundamental pedigree, (5) analysis of optical value, (6) analysis of reversion of A/P and analysis of L/R unbalance, (7) analysis of special frequency, (8) analysis of different frequency, (9) analysis of continuum frequency, (10) analysis of optimal frequency, (11) analysis of space distribution of S pedigree power, (12) analysis of single-frequency power and distribution of its correspondinrelative value (L/R), (13) analysis of the distribution of mean power, (14) analysis of the relative value A/P and L/R of power, (15) analysis of the curve of long temporal S pedigree, (16) analysis of the curve of long temporal dominant spectrum lines, (17) analysis of the curve of long temporal fundamental pedigree, (18) analysis of the curve of long temporal space distribution of power, (19) analysis of the curve of long temporal entropy, (20) analysis of the curve of long temporal special frequency, (21) analysis of the curve of long temporal continuum frequency, (22) analysis of the curve of long temporal space distribution of fundamental pedigree, (23) analysis of the curve of long temporal conventional power spectrum, (24) distinguishing of long temporal event mark.

In the above four items of (7) analysis of special frequency, (8) analysis of different frequency, (9) analysis of continuum frequency and (10) analysis of optimal frequency can be named as characteristic spectrum analysis.

The above three items of (12) analysis of single-frequency power and distribution of its relative value (L/R), (13) analysis of the distribution of mean power and (14) analysis of the relative value A/P and L/R of power can be named as analysis of power distribution.

The above ten items of (15) analysis of the curve of long temporal S pedigree, (16) analysis of the curve of long temporal dominant spectrum lines, (17) analysis of the curve of long temporal fundamental pedigree, (18) analysis of the curve of long temporal space distribution of power, (19) analysis of the curve of long temporal entropy, (20) analysis of the curve of long temporal special frequency, (21) analysis of the curve of long temporal continuum frequency, (22) analysis of the curve of long temporal space distribution of fundamental pedigree, (23) analysis of the curve of long temporal conventional power spectrum and (24) distinguishing of long temporal event mark can be named as analysis of long temporal dynamic curve.

All the analysis methods of second level will be described as following.

The said (1) calculation of entropy is carried out based on the analysis of the fluctuation signals of brain wave and the method is includes:

(1) Calculate entropy according to $$H = -\sum_{k=8}^{13} p_k \lg_2 p_k,$$

in which $p_k$ is the probability of each frequency being optimal frequency in the brain wave.

(2) Calculate the total entropy from the probability distribution of all the N leads (total is n*N).

The said (2) analysis of the single-frequency competition is also based on the analysis of the fluctuation signals of brain wave and the detailed method is to accumulate the number of the same optimal frequencies in frequency fluctuations of brain wave fluctuation signals along with time changing and so as to get the probability curve of the optimal frequency.

The following analysis methods from No. (3) to (24) are all based on the analysis of S pedigree.

The analysis method of the said (3) analysis of the general pedigree of S pedigree is to present the data of the general pedigree of S pedigree acquired during S pedigree analysis with graphs.

The analysis method of the said (4) analysis of the fundamental pedigree is to analyze statistically of the S pedigree corresponding to the fundamental frequency in S pedigree. Add the values of the multiple periodic frequency thereof from 3 milli-Hz(mHz) (for example, when 3 mHz is analyzed the value of 6 mHz, 9 mHz and etc. should also be added). Meanwhile, all the leads are classified into multiple subsections such as front, rear, left, and right subsections according to the positions of the leads in the head for respective statistic analysis.

The analysis method of the said (5) analysis of the optimal value is to present the power value of the dominant frequency and its corresponding frequency according to the space position distribution of the lead.

The analysis method of the said (6) analysis of reversion of A/P and analysis of L/R unbalance is to calculate the anterior-to-posterior ratio A/P of the power value of each frequency according to the space distribution of the lead and then present the frequencies whose A/P values are more than a predetermined limited value. Meanwhile, calculate the left-to-right ratio L/R and present the frequencies whose L/R values are more than a predetermined limited value.

The analysis method of the said four items of (7) analysis of special frequency, (8) analysis of different frequency, (9) analysis of continuum frequency, (10) analysis of optimal frequency is to present the special frequency, different frequency, continuum frequency and optimal frequency of each lead according to the space distribution position of the lead.

The analysis method of the said (11) analysis of space distribution of S pedigree power is to arrange all the power values of each spectrum line in the brain wave fluctuations according to their space lead positions. Open a window in the display interface in the form of "sub-interface in interface" to select the spectrum lines. For the selected spectrum line, its power values of each lead are shown according to the space distribution position of the lead.

The analysis method of the said (12) analysis of single-frequency power and distribution of its relative value (L/R) is to add together all the power corresponding to the dominant spectrum lines D1-Dn of each lead so as to get the total power value of each lead. Then present the power value of the fundamental frequency and the left-to-right ratio (L/R) which is more than a predetermined limited value or less than the reciprocal of said predetermined limited value according to the space distribution position of the lead.

The analysis method of the said (13) analysis of the distribution of mean power is to present the mean power value of each lead according to the space distribution position of the lead.

The analysis method of the said (14) analysis of the relative value A/P and L/R of power is to calculate the anterior-to-posterior ratio and the left-to-right ratio of the power value according to the space distribution of the lead.

The analysis method of the said (15) analysis of the curve of long temporal S pedigree is to form a curve by using fluctuation value of each pedigree or each spectrum line of each lead or all leads as vertical axis and time as horizontal axis. Open a window in the display interface in the form of "sub-interface in interface" for spectrum lines or pedigree selection.

The analysis method of the said (16) analysis of the curve of long temporal dominant spectrum lines is to form a curve by using the frequency of the spectrum lines within the dominant spectrum line zone as the vertical axis and time as horizontal axis. Open a window in the display interface in the form of "sub-interface in interface" for the arrangement selection of dominant spectrum lines (D1-Dn).

The analysis method of the said (17) analysis of the curve of long temporal fundamental pedigree is to form a curve by using the fluctuation values in each time interval of the fundamental pedigree of all leads or each lead as vertical axis and time as horizontal axis. Open a window in the display interface in the form of "sub-interface in interface" for pedigree selection.

The analysis method of the said (18) analysis of the curve of long temporal space distribution of power is to form a curve by using the power value of each spectrum line of each lead as vertical axis and time as horizontal axis. Open a window in the display interface in the form of "sub-interface in interface" for spectrum line selection.

The analysis method of the said (19) analysis of the curve of long temporal entropy is to make out a curve by using entropy of all leads or each lead as vertical axis and time as horizontal axis to present the changes of entropy along with time.

The analysis method of the said (20) analysis of the curve of long temporal special frequency is to make out a curve by using the number of special frequencies appeared for each lead or all leads as vertical axis and time as horizontal axis so as to observe the changes of special frequency along with time.

The analysis method of the said (21) analysis of the curve of long temporal continuum frequency is to form a curve by using the number of continuum frequencies appeared for each lead or all leads as vertical axis respectively and time as horizontal axis so as to observe the changes of continuum frequency along with time.

The analysis method of the said (22) analysis of the curve of long temporal space distribution of fundamental pedigree is to form curves each of which is presented according to the space position distribution of the lead by using the power value of each lead which is acquired from the result of analysis of said single-frequency power and the distribution of its relative value (L/R) as vertical axis and time as horizontal axis. Open a window in the display interface in the form of "sub-interface in interface" for pedigree selection.

The analysis method of the said (23) analysis of the curve of long temporal conventional power spectrum is to form n dynamic curves by using the power values of the multiple frequencies D1-Dn selected from the conventional power spectrum which have maximal amplitudes and which are arranged in a descending order as vertical axis and time as horizontal axis.

The analysis method of the said (24) distinguishing of long temporal event mark is to distinguish the event mark signals recorded in a certain brain wave recording box and present them in the playback of brain wave signals and in the corresponding position of the time axis of various dynamic curves.

The above mentioned second level analysis includes 24 items. By selecting and combining said 24 items the solutions can be as follows:

(1) all items are used at the same time;

(2) except for item of "distinguishing of event mark", select any individual item;

(3) Use any arbitrary combination of any item except for item of "distinguishing of event mark"

(4) Combine the item of distinguishing of event mark with any one or ones of the other nine items of the items of long temporal dynamic curve analysis;

The above mentioned methods can be used to treat the brain wave signals sampled by any one lead or any combination of more leads and the operation result of any one lead or leads combination in the analysis result can also be selected to output to a terminal processor to display, print or store.

This invention also reveals a kind of apparatus for the analysis of the fluctuation signals of brain wave. It includes electrodes, digital brain wave signal amplifier or brain wave recorder, PC, data processor and terminal processor. They are linked together in sequence. The electrodes are used to sample the brain wave signals which are transmitted to the digital brain wave signal amplifier and/or brain wave recorder for data acceptance, amplification, digital/analog conversion, digital filter or/and data storage. Data in the digital brain wave signal amplifier and/or brain wave recorder will be transmitted up to PC and the data treatment and fluctuation analysis will be performed by the data processor connected with the PC. And the analytical result will be transmitted to a terminal processor for storage, display or printing.

Any lead or combination of multiple leads of any lead connection method can be selected for placing the said electrodes.

The said data processor includes such modules for the first level analysis as module for analysis of conventional power spectrum, module for analysis of the fluctuation signals of the brain wave, module for the analysis of the fluctuations of brain wave and module for analysis of S pedigree. They are connected in sequence. Data output from the former module is input to the latter module for calculation. The data processor can also include any module of the following 24 modules for performing the second level analysis. The second level analysis module accepts the result input from the first level and perform further analysis. For the convenience of description, the second analysis modules are all marked with series numbers.

Modules which are connected to the module for analysis of the power fluctuation signals of brain wave and accept its data include (1) module for analysis of entropy calculation and (2) module for analysis of single-frequency competition.

Modules which are connected to the module for analysis of supra-slow(S) pedigree and accept its data include: (3) module for analysis of the general S pedigree, (4) module for analysis of fundamental pedigree, (5) module for analysis of optical value, (6) module for analysis of reversion of A/P and analysis of L/R unbalance, (7) module for analysis of special frequency, (8) module for analysis of different frequency, (9) module for analysis of continuum frequency, (10) module for analysis of optimal frequency, (11) module for analysis of power space distribution of S pedigree, (14) module for analysis of power of single-frequency and distribution of its relative value (L/R), (13) module for analysis of the distribution of mean power, (14) module for analysis of the power relative value of A/P and L/R , (15) module for analysis of the curve of a long temporal S pedigree, (16) module for analysis of the curve of a long temporal dominant spectrum lines, (17) module for analysis of the curve of a long temporal fundamental pedigree, (18) module for analysis of the curve of a long temporal power space distribution r, (19) module for analysis of the curve of a long temporal entropy, (20) module for analysis of the curve of a long temporal special frequency, (21) module for analysis of the curve of a long temporal continuum frequency, (22) module for analysis of the curve of a long temporal space distribution of fundamental pedigree, (23) module for analysis of the curve of a long temporal conventional power spectrum, (24) module for distinguishing of long temporal event mark.

All modules for both two levels of analyses are described respectively hereinafter. Wherein, modules for the first level analysis, The said module for conventional power spectrum analysis is used to analyze the power spectrum of the time domain brain wave with the given time period so as to get the power spectrum which can be expressed as $$P(k) = \frac{1}{N}|X_N(k)|^2.$$

The said module for analysis of brain wave power fluctuation signals are used to select a window function with small side lobe amplitude and fast attenuation, which is expressed as $$\omega(n) = 0.5 - 0.5\cos\left(\frac{2\pi n}{N}\right), n = 0, 1, \ldots N - 1.$$

Cut the brain wave signal x(n) and get $x_N(n)=x(n)\omega(n)$.

Analyze the power spectrum of the above mentioned signal $x_N(n)=x(n)\omega(n)$ with T seconds as the sampling time. Processed by FFT, the frequency-domain resolution of the frequency spectrum is acquired i.e. 1/T. The power amplitude P with the maximal energy and its corresponding frequency f are selected. The time domain brain wave signal are divided with the total time length of N seconds into subsections with the interval of T seconds in time sequence. Then carry out the said x module for conventional power analysis and module for analysis of power fluctuation signal of brain wave in order to get the time fluctuation signal of the maximal power amplitude p(n) and its corresponding frequency fluctuation signal f(n),n=1 . . . n, n=N/T.

The said module for analysis of the fluctuations of the brain wave is used to analyze the fluctuation signal of maximal power amplitude with the length of n points which is expressed as p(n). Multiply said p(n) with Hanning window with the length of n and then analysis of power spectrum is carried out. Since the unit of the time length is N seconds, frequency domain resolution is 1/N Hz. The spectrum lines within a certain frequency zone are selected from the analysis result of the power spectrum to form the fluctuations of brain wave. If the whole sampling time is more than N seconds, it will be divided into subsections with N seconds as the unit and said module for analysis of conventional power spectrum the module for analysis of the power fluctuation signals of brain wave and the module for analysis of fluctuations of the brain wave are performed for each subsection.

The said module for S pedigree analysis is used to find out several dominant spectrum lines D1-Dn with the maximal amplitude from the fluctuations of brain wave of each lead which are arranged in a descending order . In this way, S pedigree with single lead data can be obtained, totally n values. For all N leads, there are N*n dominant lines. By adding together all the dominant 1 lines with the same frequency the general pedigree of S pedigree can be obtained.

Modules for the second level analysis are described respectively hereinafter.

The data acquired from the result of the analysis performed by the module for analysis of brain wave power fluctuations signals for first level analysis are transmitted to (1) module for calculation of entropy and (2) module for analysis of single-frequency competition to perform the second level analysis. wherein, The said module for entropy calculation is used to calculate entropy according to $$H = -\sum_{k=8}^{13} p_k \lg_2 p_k,$$

in which $p_k$ is the probability of each frequency being optimal frequency in the brain wave and to calculate the total entropy from the general probability distribution of all the N leads (total is n*N)

The said module for single-frequency competition analysis is used to accumulate the number of the same optimal frequencies in frequency fluctuations of brain wave fluctuation signals along with time changing (1-n data sections) so as to get the probability curve of the optimal frequency.

Data from module for S pedigree analysis for the first level analysis is transmitted to the modules for the second level analysis.

The analysis module of the said (3) module for analysis of the general pedigree of S pedigree is to present the data of the general pedigree of S pedigree acquired during S pedigree analysis with graphs.

The analysis module of the said (4) module for analysis of the fundamental pedigree is to analyze statistically the S pedigree corresponding to the fundamental frequency in S pedigree. Add the values of the multiple periodic frequency thereof when the frequency is higher than 3 mHz, 3 mHz is included (for example, when 3 mHz is analyzed, the value of 6 mHz, 9 mHz and etc. should also be added). Meanwhile, all the leads are classified into multiple subsections such as front, rear, left, and right subsections according to the positions of the leads in the head for respective statistical analysis.

The analysis module of the said (5) module for analysis of the optimal value is to present the power value of the dominant frequency and its corresponding frequency according to the space position distribution of the lead.

The analysis module of the said (6) module for analysis of reversion of A/P and for analysis of L/R unbalance is to calculate the anterior-to-posterior ratio A/P of the power value of each frequency according to the space distribution of the lead and then present the frequencies whose A/P values are more than a predetermined limited value. Meanwhile, calculate the left-to-right ratio L/R and present the frequencies whose L/R values are more than a predetermined limited value.

The analysis module of the said four modules which include (7) module for analysis of special frequency, (8) module for analysis of different frequency, (9) module for analysis of continuum frequency, (10) module for analysis of optimal frequency are used to present the special frequency, different frequency, continuum frequency and optimal frequency of each lead according to the space distribution position of the lead respectively.

The analysis module of the said (11) module for analysis of power space distribution of S pedigree is to arrange all the power values of each spectrum line in the brain wave fluctuations according to their space lead positions. A window is opened in the display interface in the form of "sub-interface in interface" to select the spectrum lines. For the selected spectrum line, r its power values of each lead are shown according to the space distribution position of the lead.

The analysis module of the said (14) module for analysis of power of single-frequency and distribution of its relative value (L/R) is to add together all the power values corresponding to the dominant spectrum lines D1-Dn of each lead so as get the total power value of each lead. Then present the power value of the fundamental frequency and the left-to-right ratio (L/R) which is more than a predetermined limited value or less than the reciprocal of said predetermined limited value according to the space distribution position of the lead.

The analysis module of the said (13) module for analysis of the distribution of mean power is to present the mean power value of each lead according to the space distribution position of the lead.

The analysis module of the said (14) module for analysis of the power relative value A/P and L/R is to calculate the anterior-to-posterior ratio and the left-to-right ratio of the power value according to the space distribution of the lead.

The analysis module of the said (15) module for analysis of the curve of long temporal S pedigree is to form a curve by using fluctuation value of each pedigree or each spectrum line of each lead or all leads as vertical axis and time as horizontal axis. A window is opened in the display interface in the form of "sub-interface in interface" for spectrum lines or pedigree selection.

The analysis module of the said (16) module for analysis of the curve of long temporal dominant spectrum lines is to form a curve by using the frequency of the spectrum lines within the dominant spectrum line zone as the vertical axis and time as horizontal axis. And a window is opened in the display interface in the form of "sub-interface in interface" for the arrangement selection of dominant spectrum lines (D1-Dn) .The analysis module of the said (17) module for analysis of the curve of long temporal fundamental pedigree is to form a curve by using the fluctuation values in each time interval of the fundamental pedigree of all leads or each lead as vertical axis and time as horizontal axis. And a window is opened in the display interface in the form of "sub-interface in interface" for pedigree selection. The analysis module of the said (18) module for analysis of the curve of long temporal space distribution of power is to form a curve by using the power value of each spectrum line of each lead as vertical axis and time as horizontal axis. And a window is opened in the display interface in the form of "sub-interface in interface" for spectrum line selection.

The analysis module of the said (19) module for analysis of the curve of long temporal entropy is to form a curve by using entropy of all leads or each lead as vertical axis and time as horizontal axis to present the changes of entropy along with time.

The analysis module of the said (20) module for analysis of the curve of long temporal special frequency is to form a curve by using the number of special frequencies appeared for each lead or all leads as vertical axis and time as horizontal axis so as to observe the changes of special frequency along with time.

The analysis module of the said (21) module for analysis of the curve of long temporal continuum frequency is to form a curve by using the number of continuum frequencies appeared for each lead or all leads as vertical axis respectively and time as horizontal axis so as to observe the changes of continuum frequency along with time.

The analysis module of the said (22) module for analysis of the curve of long temporal space distribution of fundamental pedigree is to form curves each of which is presented according to the space position distribution of the lead by using power value of each lead which is acquired from the result of analysis of said single-frequency power and the distribution of its relative value (L/R) as vertical axis and time as horizontal axis. And a window is opened in the display interface in the form of "sub-interface in interface" for pedigree selection.

The analysis module of the said (23) module for analysis of the curve of long temporal conventional power spectrum is to form n dynamic curves by using the power values of the multiple frequencies D1-Dn selected from the conventional power spectrum which have maximal amplitude and which are arranged in a descending order as vertical axis and time as horizontal axis.

The analysis module of the said (24) module for distinguishing of long temporal event mark is used to recognize the event mark signals recorded in a certain brain wave recorder and present them in the playback of brain wave signals and present them in the corresponding position of the time axis of various dynamic curves. It can be connected to each long temporal analysis module respectively.

Data of brain wave signal of any lead or any combination of multiple leads sampled by the electrodes can be selected for treating by the said data processor.

The above mentioned modules for the second level analysis can be performed at the same time or it is also applicable to perform any combination of the said modules selected from said module (1)~module (23) except for module (24) i.e. module for distinguishing of event mark.

The above-mentioned analysis methods can be used to treat data sampled by one lead or combination of multiple leads. The operation result of one lead or combination of multiple leads can also be selected from the analysis result and be output to the terminal processor.

The said terminal processor includes display, printer and storage apparatus such as hardware disk, floppy disk and compact disk etc, which is used to accept the signals from data processor and select the operation result of one lead or combination of more leads from data processor to store, display and print.

According to the method and apparatus of the present invention, the data and curve displayed which has been inspected and calculated can be used to analyze the situation of the brain function and neurotransmitter in the patients' brain, and can also be used to analyze the functional changes of the brain which is impossible for CT and NMR. It provides direct and objective index for the diagnosis of functional encephalopathy in the medical field and make up the blank of objective inspective index in functional encephalopathy such as lunacy in the medical field.

Wherein, if the blocks are connected by arrowhead, it means logic relations. In this condition, data acquired in the anterior module is the basis of the operation of the latter module. That's to say, the latter module relies on the result of the anterior module. If the blocks are connected by beeline, it means inclusion relation. In this case, modules in the anterior blocks are composed of the latter modules. If the anterior block are connected by dashed, it means the anterior shows only the general name of the sort of the latter modules' attributes.

DETAILED DESCRIPTION OF THE PREFERRED EMBODIMENT

Further description is given in the combination of the drawings hereinafter.

The process of analyzing the brain wave fluctuations includes: getting the brain wave fluctuation signals from the brain wave with computer fluctuation scanning technique, then analyzing of the frequency spectrum of the fluctuation signals in order to get the power spectrum within the scope of 1 to 255 mHz. The detailed analysis process can be summarized as: dividing the 1024 seconds brain wave data into 512 subsections each of which is with 2 seconds, analyzing the power spectrum of data of each subsection and select the maximal power amplitude within the scope of 0.5 to 50 Hz, analyzing the power spectrum of the time fluctuations of the maximal power amplitude (that is the maximal values of the corresponding power spectrums of said 521 subsections) so as to get the fluctuations of the power spectrum within the scope of 1 to 255 mHz.

There are three types of structure of the apparatus according to the present invention, which are as follows.

Figures 1, 2:
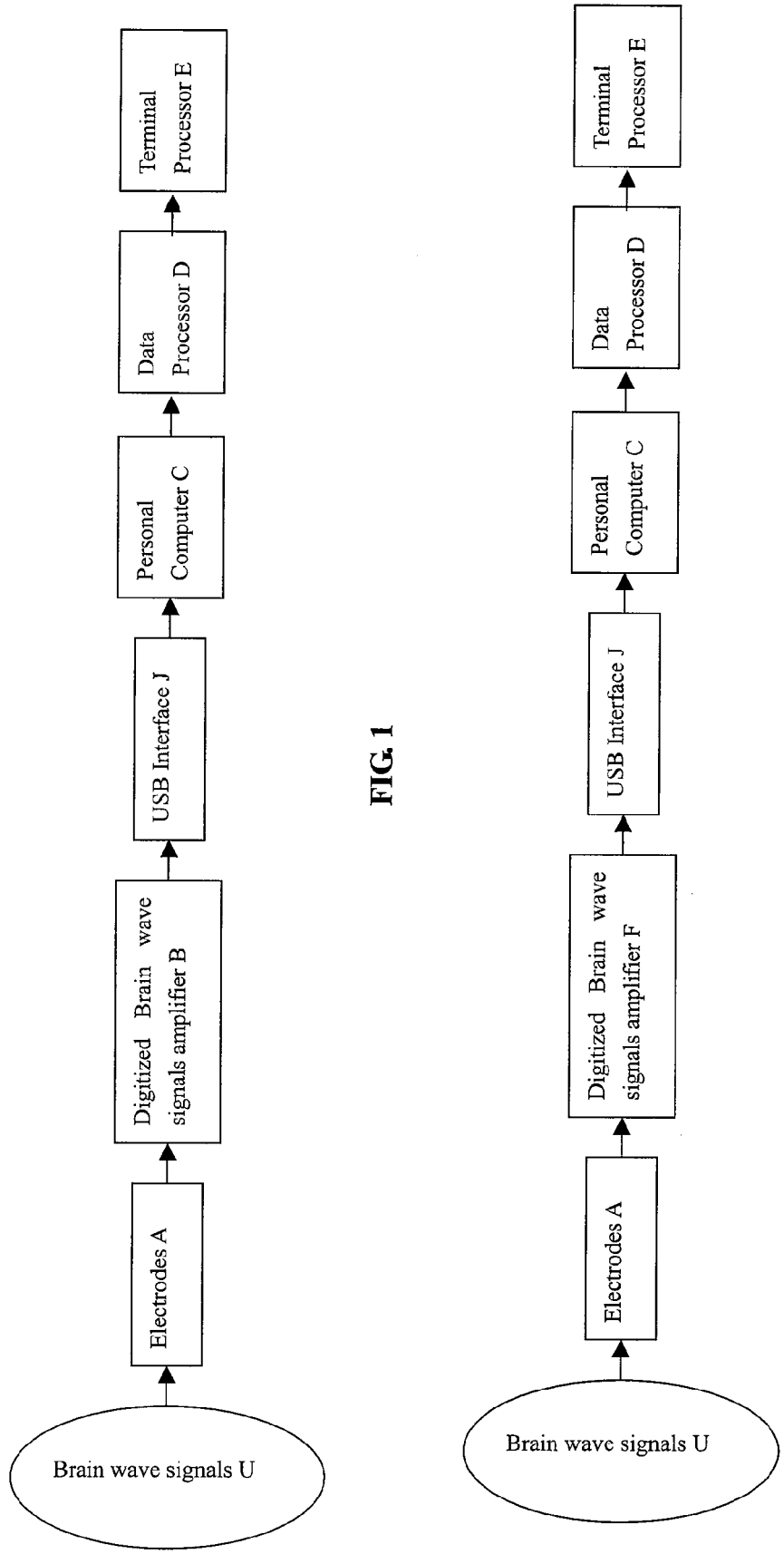
FIG. 1 is a block diagram according to a first embodiment of the present invention.
FIG. 2 is a block diagram according to a second embodiment of the present invention.

As shown in FIG. 1, it includes electrodes A, a digitized brain wave amplifier B, a USB interface J, a Personal Computer C, a data processor D and a terminal processor E, which are connected in turn.

As shown in FIG. 2, it includes electrodes A, a brain wave recorder F, a USB interface J, a PC C, a data processor D and a terminal processor E, which are connected in turn.

Figure 3:
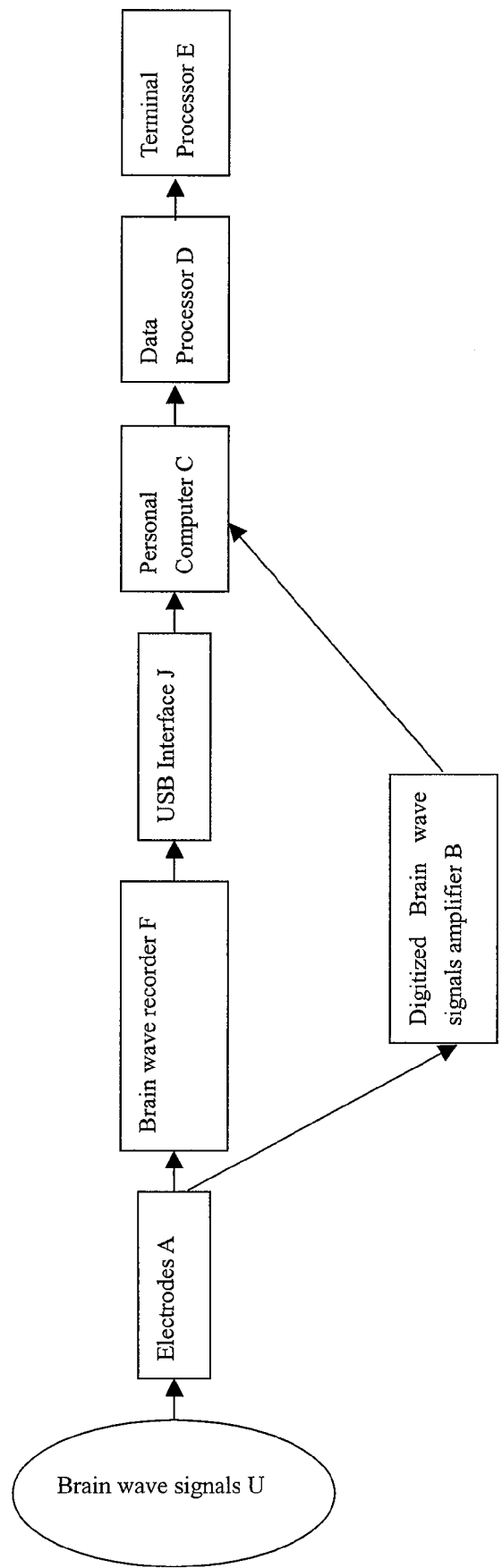
FIG. 3 is a block diagram according to a third embodiment of the present invention.
Figure 4:
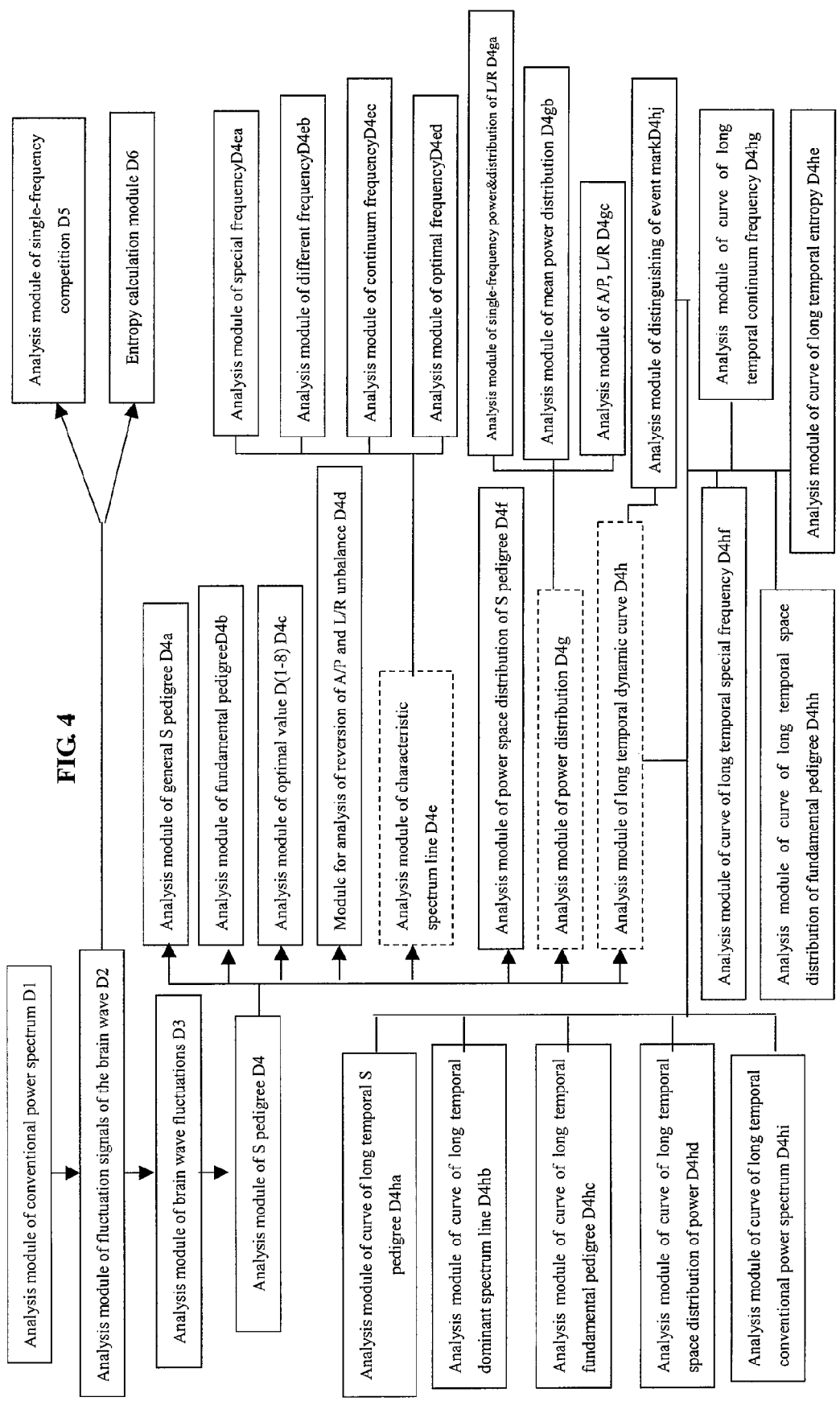
FIG. 4 is a block diagram showing structures of a data processor of the present invention.

As shown in FIG. 3, it includes an electrode A, a digital brain wave amplifier B and a brain wave recorder F, a USB interface J, a PC C, a data processor D and a terminal processor E, which are connected in turn. Wherein, the electrode A is connected to the digital brain wave amplifier B and the brain wave recorder at the same time. The digital brain wave signal amplifier B is connected to the PC C, and the brain wave recorder F is connected to the PC C through the USB interface J. Finally, the PC C is connected to the data processor D and the terminal processor E in sequence.

The functions of each component in the present invention are described below.

The electrode A is used to sample brain wave signals. Location of the electrode complies with the 12 leads international standard lead system with the position separately in F3, F4, C3, C4, P3, P4, O1, O2, F7, F8, T5, T6. Frequency of brain sampling is 128 Hz.

The digital brain wave signal amplifier B has functions of accepting signals, signal amplification, digital/analog conversion and data filter etc.

The brain wave recorder F is used to sample and analyze long temporal (longer than 18 min) brain wave data. It has functions of signal sampling, signal amplification, digital/analog conversion and data filter, data storage and data playback etc. Data in the brain wave recorder is uploaded to PC for fluctuation analysis.

The PC C is configured to have a PIV host and 256 M EMS memory.

The terminal processor E is composed of display, printer and storage devices such as hardware disk, floppy disk and compact disk. It accepts data from the data processor D for display, storage or print.

The data processor D includes an analysis module of module for a first level conventional power spectrum power D1, an analysis module of fluctuation signals of brain wave D2, an analysis module of fluctuation of brain wave D3 and an analysis module of S pedigree D4. They are connected to each other in sequence. And data output from the anterior module is transmitted to the latter module for analysis. The data processor can also include any module of the 24 modules for the second level analysis. For the convenience of description, the second level analysis modules are all marked with series number.

Modules which are connected to module D2 and accept its data are: (1) an analysis module of entropy calculation D5 and (2) an analysis module of single-frequency competition D6.

Modules which are connected to module D4 and accept its data are: (3) an analysis module of the general pedigree of S pedigree (i.e. module for analysis of the general pedigree of S pedigree, and for the other modules) D4$a$, (4) an analysis module of fundamental pedigree D4$b$, (5) an analysis module of optical value D4$c$, (6) an analysis module of the reversion of A/P; analysis module on L/R unbalance D4$d$, (7) an analysis module of special frequency D4$ea$, (8) an analysis module of different frequency D4$eb$, (9) an analysis module of continuum frequency D4$ec$, (10) an analysis module of optimal frequency D4$ed$, (11) an analysis module of space distribution of S pedigree power D4$f$, (12) an analysis module of power distribution of single-frequency D4$ga$, (13) an analysis module of the distribution of mean power D4$gb$, (14) an analysis module of the relative value A/P and L/R of power D4$gc$, (15) an analysis module on the curve of long temporal S pedigree D4$ha$, (16) an analysis module of the curve of long temporal optical lines D4$hb$, (17) an analysis module of the curve of long temporal fundamental pedigree D4$hc$, (18) an analysis module of the curve of long temporal space distribution of power D4$hd$, (19) an analysis module of the curve of long temporal entropy D4$he$, (20) an analysis module of the curve of long temporal special frequency D4$hf$, (21) an analysis module of the curve of long temporal continuum frequency D4$hg$, (22) an analysis module of the curve of long temporal space distribution of fundamental pedigree D4$hh$, (23) an analysis module of the curve of long temporal conventional power spectrum D4$hi$, (24) a distinguishing module of long temporal event mark D4$hj$.

Based on S pedigree analysis, (3) analysis of the general pedigree of S pedigree, (4) analysis of fundamental pedigree, (5) analysis of optical value, (6) reversion of A/P; analysis of L/R unbalance, (7) analysis of special frequency, (8) analysis of different frequency, (9) analysis of continuum frequency, (10) analysis on optimal frequency, (11) analysis of space distribution of S pedigree power, (12) power of single-frequency and distribution of its corresponding value (L/R), (13) analysis of the distribution of mean power, (14) analysis of the relative value A/P and L/R of power, (15) analysis of the curve of long temporal S pedigree, (16) analysis of the curve of long temporal optical lines, (17) analysis of the curve of long temporal fundamental pedigree, (18) analysis of the curve of long temporal space distribution of power, (19) analysis of the curve of long temporal entropy, (20) analysis of the curve of long temporal special frequency, (21) analysis of the curve of long temporal continuum frequency, (22) analysis of the curve of long temporal space distribution of fundamental pedigree, (23) analysis of the curve of long temporal conventional power spectrum, (24) distinguishing of long temporal event mark.

Wherein, the above (7) analysis module of special frequency D4$ea$, (8) analysis module of different frequency D4$eb$, (9) analysis module of continuum frequency D4$ec$, (10) analysis module of optimal frequency D4$ed$ are integrated as an analysis module of characteristic lines D4$e$.

The above (12) analysis module of power distribution of single-frequency D4$ga$, (13) analysis module of the distribution of mean power D4$gb$, (14) analysis module of the relative value AJP and L/R of power D4$gc$ are integrated as an analysis module of power distribution D4$g$.

The above ten modules including (15) the analysis module of the curve of long temporal S pedigree D4$ha$, (16) the analysis module of the curve of long temporal optical lines D4$hb$, (17) the analysis module of the curve of long temporal fundamental pedigree D4$hc$, (18) the analysis module of the curve of long temporal space distribution of power D4$hd$, (19) the analysis module of the curve of long temporal entropy D4$he$, (20) the analysis module of the curve of long temporal special frequency D4$hf$, (21) the analysis module of the curve of long temporal continuum frequency D4$hg$, (22) the analysis module of the curve of long temporal space distribution of fundamental pedigree D4$hh$, (23) the analysis module of the curve of long temporal conventional power spectrum D4$hi$, (24) the distinguishing module of long temporal event mark D4$hj$ are integrated as an analysis module of long temporal dynamic curve D4$h$.

The functions of each module are described as below.

1. Analysis Module of Conventional Power Spectrum D1

Carry out Fourier Transformation directly to the observation data $X_N(n)$ which has N sampling points of brain wave, with the result of $X_N(e^{j\omega})$. Make a square of its amplitude which is then divided by N. The result is the estimate value of the real power spectrum $P(e^{j\omega})$ of x(n) The power spectrum estimated with cyclogram can be expressed as $$P(e^{j\omega}) = \frac{1}{N}|X_N(\omega)|^2.$$

Calculation of $X_N(\omega)$ is acquired by using fast Fourier Transformation $$X_N(k) = \sum_{n=0}^{N-1} x(n)W_N^{nk}, k = 0, 1, \ldots, N-1, W_N = e^{-j\frac{2\pi}{N}}.$$

And the power spectrum can be expressed as $$P(k) = \frac{1}{N}|X_N(k)|^2.$$

Analyze the power spectrum of a wave signal in the time domain and the given time length is 8 s so as to get the energy distribution in the frequency domain i.e. conventional power spectrum. Then transmit the power spectrum to the terminal processor E in the form of graph.

2. Analysis Module of Fluctuation Signals of Brain Wave Power D2

During process of the real power estimation practice, the window function with small major side lobe amplitude and fast attenuation should be selected. The major lobe of Hanning window is relatively wide, but it has small side lobe and high attenuation speed. It can be expressed as $$\omega(n) = 0.5 - 0.5\cos\left(\frac{2\pi n}{N}\right),$$
$$n = 0, 1, \ldots N - 1.$$

Cutting the data with Hanning window, the result is $X_N(n)=x(n)\omega(n)$.

Multiplying the time domain brain wave signal of a given length of 2s with Hanning window, and analyze the power spectrum of the product. Since the sampling time is 2 s, perform operation of FFT and the frequency resolution of the frequency spectrum is obtained, which is $1/T=½=0.5Hz$ (T is the sampling time). Select the power amplitude p with maximal energy and its corresponding frequency f within the frequency zone from 8 Hz to 13 Hz (8 Hz, 8.5 Hz, 9 Hz, 9.5 Hz, 10 Hz, 10.5 Hz, 11 Hz, 11.5 Hz, 12 Hz, 12.5 Hz, 13 Hz, totally including 11 values ).

Divide the 1024 seconds brain wave data in time sequence into 512 subsections each of which is of 2 seconds . Perform the analysis module of conventional power spectrum D1 and analysis module of the brain wave fluctuation signals D2 to get the time fluctuation signals of the maximal power amplitude p(n) and its corresponding frequency fluctuation signals f(n), n=1 . . . 512. It presents the fluctuation process of the power and its corresponding maximal amplitude within 1024 seconds.

Transmit the time fluctuation signals to analysis module of fluctuation signals of brain wave D3, analysis module of entropy calculation D5 and analysis module of single-frequency competition D6. And transmit it to the terminal processor E at the same time.

3. Analysis Module of Brain Wave Fluctuations D3

Analyze the fluctuation signals p(n) of the maximal power amplitude within the length of 1024 s which is of 512 points. Multiply it with Hanning window with the length of 512 and then carry out the analysis of power spectrum. Since the unit of the time length is 1024 seconds, the frequency domain resolution is $1/1024$ Hz. The spectrum lines within the frequencies of $1/1024*(1$ to 255) Hz from the analysis result of the power spectrum form the fluctuations of brain wave. If the whole sampling time is more than 1024 seconds, divide it into subsection with 1024 seconds as the unit and then carry out the said analysis module of conventional power spectrum D1, analysis module of the fluctuation signals of brain wave power D2 and analysis modules of fluctuations of the brain wave D3 for each subsection repeatedly.

The analysis module of brain wave fluctuations D3 will transmit the fluctuations signals of brain wave to the analysis module of S pedigree D4 and also to the terminal processor E.

4. Analysis Module of S Pedigree D4

Find out 8 dominant lines D1-D8 with maximal amplitude from the fluctuations of brain wave of each lead and arrange them by a descending order so as to get the single lead S pedigree with 8 values. And for all 12 leads, there are 12×8=96 dominant spectrum lines. Add together the number of dominant spectrum lines with the same frequency, and then the general pedigree of S pedigree is obtained.

Analysis module of S pedigree D4 transmits the signals of single-lead S pedigree and general S pedigree to analysis module on the general peigree of S pedigree D4a, analysis module of fundamental pedigree D4b, analysis module of optical value D (1-8) D4c, module for analysis of the reversion of A/P and L/R unbalance D4d, analysis module of characteristic lines D4e, analysis module of space distribution of pedigree power D4f, analysis module of power distribution D4g and analysis module of long temporal dynamic curve D4h. It also transmits signals of general S pedigree to the terminal processor E.

5. Entropy Calculation Module D5

Calculate entropy according to $$H = -\sum_{k=8}^{13} p_k \lg_2 p_k,$$

in which $P_k$ is the probability of each frequency being optimal in the brain wave (the total number is 512 and the probability is the optimal number of each frequency being divided by 512). Calculate the total entropy from the distribution of the probabilities of all 12 leads (total number is 512*12 )and the data is transmitted to the terminal processor E.

6. Analysis Module of Single-Frequency Competition D6 accumulate the number of the same optimal frequencies in frequency fluctuations f(n) of brain wave fluctuation signals along with time changing (1-512 subsections) so as to get the optimal probability curve.

7. Analysis Module of General Pedigree of S Pedigree D4a

Form a graph of to present the general S pedigree signals produced by analysis module of S pedigree D4 and then the data and the graph are transmitted to the terminal processor E.

8. Analysis Module of Fundamental Pedigree D4b

Analyze statistically the pedigrees of S1, S2, S3, S4, S5, S6, S7,S11, S13 which is corresponding to the nine fundamental frequencies of 1 milli-Hz 2 milli-Hz, 3 milli-Hz, 4 milli-Hz, 5 milli-Hz, 6 milli-Hz, 7 milli-Hz, 11 milli-Hz, 13 milli-Hz in S pedigree respectively. When the frequency is higher than 3 milli-Hz(3 milli-Hz is included), the values of the multiple frequency should also be accumulated(for example, when 3 milli-Hz is statistically analyzed, the values of 6 mHz, 9 mHz should also be accumulated). Meanwhile, according to their positions in the brain, the 12 leads are divided into four sections to perform the statistical analysis, namely left anterior (F3, F7, C3) ,left posterior (T5, P3, O1), right anterior (F4, C4, F8), right posterior (P4, T6, O2) . The result is transmitted to the terminal processor E.

9. Analysis Module of Optimal Value (D1-D8) D4c

Present the power values of the dominant frequencies D1-D8 and their corresponding frequency in each lead according to the space position distribution of the lead and transmit the result to the terminal processor E.

10. Module for Analysis of Reversion of A/P and L/R Unbalance D4d

Said module D4d is to calculate the anterior-to-posterior A/P (such as F3/C3, C3/P3) of the power value of each frequency according to the space distribution of the lead and then present the frequencies whose A/P values are more than 10. Meanwhile, calculate the left-to-right ratio L/R (such as F3/F4, C3/C4) and present the frequencies whose L/R values are more than 10.

11. Analysis Module of Characteristic Spectrum Line D4$e$

The said module D4$e$ includes analysis module of special frequency D4$ea$, analysis module of different frequency D4$eb$, analysis module of continuum frequency D4$ec$ and analysis module of optimal frequency D4$ed$, wherein:

(1) analysis module of special frequency D4$ea$ is to present the special frequency for each lead according to the space distribution position of the lead and the result is transmitted to the terminal processor E.

(2) analysis module of different frequency D4$eb$ is to present the different frequency for each lead according to the space distribution position of the lead and the result is transmitted to the terminal processor E.

(3) analysis module of continuum frequency D4$ec$ is to present the continuum frequency for each lead according to the space distribution position and the result is transmitted to the terminal processor E.

(4) analysis module of optimal frequency D4$ed$ is to present the optimal frequency for each lead according to the space distribution position of the lead and the result is transmitted to the terminal processor E.

12. Analysis Module of Power Space Distribution of S Pedigree D4$f$

Select a certain spectrum line with a given frequency from the fluctuations of brain wave and present the power value of each lead according to the space position distribution of the lead. Then the power space distribution is transmitted to the terminal processor E.

13. Analysis module of power distribution D4$g$ which includes analysis module of single-frequency power and distribution of the corresponding relative value (L/R) D4$ga$, analysis module of the mean power distribution D4$gb$ and analysis module of A/P, L/R D4$gc$.

Add the power values corresponding to the optimal spectrum lines D1-D8 for each lead so as to get the total power value of each lead. The results are transmitted respectively to analysis module of single-frequency power and distribution of the corresponding relative value (L/R) D4$ga$, analysis module of the mean power distribution D4$gb$ and analysis module of A/P, L/R D4$gc$.

(1) analysis module of single-frequency power and distribution of the corresponding relative value (L/R) D4$ga$: present the values of fundamental frequency power and L/R ratio which is more than 10 or less than 0.1 according to the space distribution of the lead and the result is transmitted to the terminal processor E.

(2) analysis module of the mean power distribution D4$gb$: present the mean power of each lead according to the space distribution of the lead and the result is transmitted to the terminal processor E.

(3) analysis module of A/P, L/R D4$gc$: calculate the anterior-to-posterior ratio (such as F3/C3, C3/P3) and left-to-right ratio (such as F3/F4, C3/C4) of the power value according to space distribution of the lead and the result is transmitted to the terminal processor E.

14. Analysis Module of Long Temporal Dynamic Curve D4$h$

Said module D4$h$ includes analysis module of the curve of long temporal S pedigree D4$ha$, analysis module of the curve of long temporal dominant spectrum lines D4$hb$, analysis module of the curve of long temporal fundamental pedigree D4$hc$, analysis module of the curve of long temporal space distribution of power D4$hd$, analysis module of the curve of long temporal entropy D4$he$, analysis module of the curve of long temporal special frequency D4$hf$, analysis module of the curve of long temporal continuum frequency D4$hg$, analysis module of the curve of long temporal space distribution of fundamental pedigree D4$hh$, analysis module of the curve of long temporal conventional power spectrum D4$hi$, distinguishing module of long temporal event mark D4$hj$.

Divide the long temporal (with sampling time longer than 18 min) brain wave data into subsections according to the time length of 18 minutes and analyze the fluctuations of brain wave for each subsection (repeat the procedures from D1 to D4) The result is transmitted to the following analysis modules.

(1) analysis module of the curve of long temporal dominant spectrum lines D4$hb$ is to form a curve by, using the frequency of the spectrum lines within the dominant spectrum line zone as the vertical axis and time as horizontal axis. A sub-interface or sub-window is provided in the display interface in the form of "sub-interface in interface" for arrangement selection of optimal lines (D1-Dn) while displaying the curve of the curve of long temporal dominant spectrum lines.

(2) analysis module of the curve of S pedigree D4$hb$ is to form a curve by using fluctuation values of each pedigree or each spectrum line of each lead or all leads as vertical axis and time as horizontal axis so as to observe the changes of each frequency spectrum or pedigree in the whole brain along with time. A sub-interface or sub-window is provided in the display interface in the form of "sub-interface in interface" for spectrum lines or pedigree selection while displaying the curve of S pedigree.

(3) The analysis module of the curve of long temporal fundamental pedigree D4$hc$ is to form a curve by using the fluctuation values in each time interval of the fundamental pedigree of all leads or each lead as vertical axis and time as horizontal axis so as to master the dynamic information of several fundamental pedigrees which have close relations to the brain's function. A sub-interface or sub-window is provided in the display interface in the form of "sub-interface in interface" for pedigree selection while displaying the curve of long temporal fundamental pedigree.

(4) The analysis module of the curve of long temporal space distribution of power D4$hd$ is to form a curve by using the power value of each spectrum line of each lead as vertical axis and time as horizontal axis so as to observe the changes of power value for each line in the lead along with time. A window is opened in the display interface in the form of "sub-interface in interface" for spectrum line selection, A sub-interface or sub-window is provided in the display interface in the form of "sub-interface in interface" for spectrum line selection while displaying the curve of long temporal space distribution of power.

(5) analysis module on the curve of long temporal entropy D4$he$: Form a curve by using the entropy of each lead or all leads as vertical axis and time as horizontal axis, to present the changes of entropy along with time so as to observe energy distribution of the brain in different time.

(6) analysis module of the curve of long temporal special frequency D4$hf$: Form a curve by using the number of special frequencies of all leads as vertical axis and time as horizontal axis so as to observe the dynamic changes of special frequency along with time.

(7) analysis module of the curve of long temporal continuum frequency D4$hg$: Form a curve by using the number of different frequencies in each lead or all leads as vertical axis and time as horizontal axis to observe decrease of patents' brain functions in different period.

(8) The analysis module of the curve of space distribution of fundamental pedigree is to form curves each of which is presented according to the space position distribution of the lead by using power value of each lead which is acquired from the result of module for analysis of single-frequency power and the distribution of its corresponding relative value (L/R) D4*ga* as vertical axis and time as horizontal axis. A sub-interface or sub-window is provided in the display interface in the form of "sub-interface in interface" for pedigree selection while displaying the curve of space distribution of fundamental pedigree. So as to observe the changes of each fundamental pedigree along with time and space distribution.

(9) the analysis module of the curve of conventional power spectrum D4*hi* is to form 8 dynamic curves by using power values of 8 frequencies D1-D8 which are arranged from big to small and selected from the conventional power spectrum which have maximal amplitudes and which are arranged in a descending order as vertical axis and time as horizontal axis so as to observe the changes of optical frequencies in the brain wave along with time.

(10) The analysis module of distinguishing of event mark D4*hj* is connected to each of the long temporal analysis modules respectively and it is applied to distinguish the event mark signals recorded in the brain wave recorder and present them in the playback of brain wave signals and the corresponding position on the time axis of various dynamic curves.

INDUSTRIAL APPLICATION

According to methods and apparatus of the present invention, the data and curve, obtained by inspecting and calculating, can be used to analyze the situation of the brain function and neurotransmitter in the patents' brain. It can also be used to analyze the functional changes of the brain which is impossible for CT and NMR, and thus it can provide direct and objective index for the diagnosis of functional encephalopathy in the medical field and make up the blank of objective inspective index in functional encephalopathy such as lunacy in the medical field.

What is claimed is:

1. A method for brain wave fluctuations analysis performed using computer techniques, comprising:
   providing multiple leads for acquiring brain wave signals;
   dividing the brain wave signals within a first predetermined period into subsections with a predetermined sampling time;
   using a data processor, analyzing the power spectrum of brain wave signal in each said subsection to acquire energy distribution thereof in frequency domain;
   analyzing the fluctuations of brain wave signal in each said subsection according to said energy distribution to select a maximal power amplitude and a corresponding frequency thereof; and
   forming a fluctuation signal of maximal power amplitude and a fluctuation signal of corresponding frequency by use of all maximal power amplitudes and corresponding frequencies thereof in subsections.

2. The method according to claim 1, further comprising:
   cutting the brain wave signal in each subsection by multiplying the said brain wave signal with a selected window function that has a small side lobe amplitude and a fast attenuation;
   analyzing the power spectrum of said cut brain wave in each said subsection to acquire the energy distribution thereof in the frequency domain;
   analyzing the fluctuations of said cut brain wave signal in each said subsection according to said energy distribution to select a maximal power amplitude and a corresponding frequency thereof; and
   forming a fluctuation signal of maximal power amplitude and a fluctuation signal of corresponding frequency with respect to said cut brain wave signal by use of all maximal power amplitudes and corresponding frequencies thereof in subsections.

3. The method according to claim 2, wherein said selected window function is $$\omega(n) = 0.5 - 0.5\cos\left(\frac{2\pi n}{N}\right),$$
$$n = 0, 1, \ldots N - 1.,$$

wherein n represents sampling point, N represents amount of sampling points in the predetermined time period.

4. The method according to claim 3, further comprising:
   analyzing the power spectrum of the product of said fluctuation signal of maximal power amplitude with respect to the brain wave signal and a selected window function; and
   forming a brain wave fluctuations by selecting spectrum lines within a predetermined frequencies from said analysis of said power spectrum of the product.

5. The method according to claim 4, further comprising:
   selecting multiple dominant spectrum lines with maximal amplitude from the brain wave fluctuations of each lead respectively; and
   sorting said multiple dominant spectrum lines according to the value of amplitude by the order of descending to form a supra-slow pedigree of the brain wave sampled by a single lead.

6. The method according to claim 5, further comprising:
   selecting dominant spectrum lines with a same frequency from all the dominant spectrum lines of said leads; and
   accumulating said selected dominant spectrum lines with a same frequency to form a general pedigree of said supra-slow pedigree.

7. The method according to claim 6, further comprising presenting the data of said general supra-slow pedigree with graphs.

8. The method according to claim 6, further comprising the step of counting times that a power corresponding to each fundamental frequency becomes an optimal value for each lead.

9. The method according to claim 8, wherein the power of the fundamental frequency is obtained by adding up that of multiple periodic frequencies of the fundamental frequency if the fundamental frequency is not less than 3 mHz.

10. The method according to claim 6, further comprising presenting the power value of the dominant frequency and a corresponding frequency according to the space position distribution of said leads.

11. The method according to claim 6, further comprising:
    calculating the anterior-to-posterior ratio and the left-to-right ratio of the power of each frequency according to the space distribution position of the leads;
    presenting the frequencies of which anterior-to-posterior ratio and left-to-right ratio are respectively more than a predetermined value.

12. The method according to claim 6, further comprising presenting the special frequency, different frequency, continuum frequency and optimal frequency of each lead according to the space distribution positions of the leads.

13. The method according to claim 6, further comprising:
   sorting the power of each spectrum line in said brain wave fluctuations according to space distribution positions of the leads; and
   providing a window in a display interface for showing the power of the spectrum line while being selected according to the space position distribution of said leads.

14. The method according to claim 6, further comprising: at least any one of the following steps:
   calculating a general power of each lead by adding up a power corresponding to each said dominate spectrum lines;
   calculating average power of each lead, and anterior-to-posterior ratio and left-to-right ratio regarding to the general power in accordance with space distribution positions of said leads;
   displaying the power of the fundamental frequencies;
   displaying the average power and left-to-right ratio within a predetermined scope in accordance with space distribution positions of said leads; and
   displaying the anterior-to-posterior ratio.

15. The method according to claim 14, wherein the predetermined scope for the left-to-right ratio is more than 10 or is less than 0.1.

16. The method according to claim 6, further comprising: the steps of
   providing a second predetermined period for sampling a brain wave signal; and
   dividing the brain wave signal within the second predetermined period into multiple sections with the first predetermined period.

17. The method according to claim 16, further comprising at least any one of the following steps:
   forming and displaying a dynamitic curve of dominant spectrum lines by use of the dominant spectrum lines acquired in each first predetermined period, parameters of which are time and frequency, respectively;
   forming and displaying a dynamitic curve of supra-slow pedigree by use of the supra-slow pedigree acquired in each first predetermined period, parameters of which are time and fluctuation value of each pedigree or each spectrum line of each lead or all leads, respectively;
   forming and displaying a dynamitic curve of fundamental pedigree by use of the fundamental pedigree acquired in each first predetermined period, parameters of which are time and the fluctuation values of the fundamental pedigree of the leads, respectively;
   forming and displaying a dynamitic curve of space distribution of power by use of the power of each spectrum line of each lead acquired in each first predetermined period, parameters of which are time and the power of each spectrum line of each lead, respectively;
   forming and displaying a dynamitic curve of entropy by use of the entropy acquired in each first predetermined period, parameters of which are time and entropy, respectively;
   forming and displaying a dynamitic curve of special frequency by use of the special frequency of each lead acquired in each first predetermined period, parameters of which are time and the number of special frequencies appeared for each lead or all leads, respectively;
   forming and displaying a dynamitic curve of continuum frequency by use of the continuum frequency of each lead acquired in each first predetermined period, parameters of which are time and the number of continuum frequencies appeared for each lead or all leads, respectively;
   forming and displaying a dynamitic curve of space distribution of fundamental pedigree by use of the space distribution of fundamental pedigree of each lead acquired in each first predetermined period, parameters of which are time and the power of each lead of the fundamental pedigree; and
   forming and displaying a dynamitic curve of power spectrum by use of the power spectrum of each lead acquired in each first predetermined period, parameters of which are time and the power of dominant frequencies of each lead.

18. The method according to claim 17, further comprising the step of:
   providing a sub-interface for selecting the spectrum lines or the spectrum pedigrees while displaying the dynamitic curves.

19. The method according to claim 18, further comprising the steps of:
   providing a means for recording event mark signals; and
   marking related parts on the dynamitic curves in accordance with the event mark signals while playing back of brain wave signals and displaying the dynamitic curves.

* * * * *